US012599290B2

(12) United States Patent
Aiba

(10) Patent No.: US 12,599,290 B2
(45) Date of Patent: Apr. 14, 2026

(54) OPTICAL CONNECTOR AND MEDICAL DEVICE

(71) Applicant: Sony Olympus Medical Solutions Inc., Tokyo (JP)

(72) Inventor: Koji Aiba, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 375 days.

(21) Appl. No.: 18/546,781

(22) PCT Filed: Oct. 20, 2021

(86) PCT No.: PCT/JP2021/038834
§ 371 (c)(1),
(2) Date: Aug. 17, 2023

(87) PCT Pub. No.: WO2022/185602
PCT Pub. Date: Sep. 9, 2022

(65) Prior Publication Data
US 2024/0298880 A1 Sep. 12, 2024

(30) Foreign Application Priority Data

Mar. 2, 2021 (JP) ................................. 2021-032492

(51) Int. Cl.
*A61B 1/00* (2006.01)
*G02B 6/32* (2006.01)

(52) U.S. Cl.
CPC ...... *A61B 1/00117* (2013.01); *A61B 1/00126* (2013.01); *G02B 6/322* (2013.01)

(58) Field of Classification Search
CPC ............ A61B 1/00117; A61B 1/00126; A61B 1/00119; A61B 1/00121; A61B 1/00128;
(Continued)

(56) References Cited

U.S. PATENT DOCUMENTS

| | | | |
|---|---|---|---|
| 5,299,066 A | 3/1994 | Rombult | |
| 2007/0212002 A1 | 9/2007 | Sato | |
| 2017/0254964 A1* | 9/2017 | Yajima | ................. G02B 6/3878 |

FOREIGN PATENT DOCUMENTS

| | | |
|---|---|---|
| CN | 203524629 U | 4/2014 |
| JP | H07-502836 A | 3/1995 |

(Continued)

OTHER PUBLICATIONS

International Search Report and Written Opinion mailed on Jan. 18, 2022, received for PCT Application PCT/JP2021/038834, filed on Oct. 20, 2021, 11 pages including English Translation.

*Primary Examiner* — Angela M. Medich
(74) *Attorney, Agent, or Firm* — XSENSUS LLP

(57) ABSTRACT

An optical connector includes an outer frame, having a cylindrical shape, into which a part of an optical transmission line for transmitting an optical signal is inserted, the outer frame covering an emission end for an optical signal of the optical transmission line; a collimator lens provided in the outer frame and facing the emission end; and a support mechanism that is disposed in the outer frame and that maintains a posture of the collimator lens in the outer frame. A positioning surface that abuts on the collimator lens to maintain the posture of the collimator lens in the outer frame is provided in the outer frame. The support mechanism includes a biasing member and a pressing member that presses the biasing member and biases the collimator lens toward the positioning surface with the biasing member.

11 Claims, 12 Drawing Sheets

(58) Field of Classification Search
CPC .... A61B 1/00165; G02B 6/322; G02B 6/327;
G02B 6/38; G02B 6/3821; G02B 6/3878;
G02B 6/3879
See application file for complete search history.

(56) References Cited

FOREIGN PATENT DOCUMENTS

| | | | |
|----|----------------|----|---------|
| JP | 2001-290086 | A | 10/2001 |
| JP | 2008-278971 | A | 11/2008 |
| JP | 2012-068535 | A | 4/2012 |
| JP | 2014-081606 | A | 5/2014 |
| JP | 2014-085474 | A | 5/2014 |
| JP | 2016-010496 | A | 1/2016 |
| JP | 2017083674 | A | 5/2017 |
| JP | 2019171158 | A | 10/2019 |
| WO | 2016/084113 | A1 | 6/2016 |
| WO | WO-2016147556 | A1 | 9/2016 |

* cited by examiner

OPTICAL CONNECTOR AND MEDICAL DEVICE

CROSS-REFERENCE TO RELATED APPLICATIONS

The present application is based on PCT filing PCT/JP2021/038834, filed Oct. 20, 2021, which claims priority to Japanese Patent Application No. 2021-032492, filed Mar. 2, 2021, the contents of each are incorporated herein by reference.

FIELD

The present disclosure relates to an optical connector and a medical device.

BACKGROUND

There has been known an optical connector that mechanically and optically connects two transmission cables in each of which an optical fiber for transmitting optical signals is disposed (e.g., see Patent Literature 1).

In such an optical connector, generally, a part of an optical fiber is disposed in a cylindrical outer frame, and a collimator lens facing an incident end or an emission end of the optical fiber is disposed.

CITATION LIST

Patent Literature

Patent Literature 1: JP 2014-85474 A

SUMMARY

Technical Problem

By the way, a change in the posture of a collimator lens in an outer frame may negatively affect the reliability of optical communication.

Therefore, an object is to provide an optical connector and a medical device capable of favorably maintaining the posture of a collimator lens and securing the reliability of optical communication.

The present disclosure has been made in view of the above, and an object thereof is to provide an optical connector and a medical device capable of favorably maintaining the posture of a collimator lens and securing the reliability of optical communication.

Solution to Problem

To solve the above-described problem and achieve the object, an optical connector according to the present disclosure includes: an outer frame, having a cylindrical shape, into which a part of an optical transmission line for transmitting an optical signal is inserted, the outer frame covering an incident end or an emission end for an optical signal of the optical transmission line; a collimator lens provided in the outer frame and facing the incident end or the emission end; and a support mechanism that is disposed in the outer frame and that maintains a posture of the collimator lens in the outer frame, wherein a positioning surface that abuts on the collimator lens to maintain the posture of the collimator lens in the outer frame is provided in the outer frame, and the support mechanism includes: a biasing member; and a pressing member that presses the biasing member and biases the collimator lens toward the positioning surface with the biasing member.

Moreover, a medical device according to the present disclosure includes: a medical observation device that images a subject and generates a captured image; two transmission cables in each of which an optical transmission line for transmitting an optical signal based on the captured image is disposed; and an optical connector that mechanically and optically connects the two transmission cables with each other, wherein the optical connector includes: an outer frame, having a cylindrical shape, into which a part of the optical transmission line is inserted, the outer frame covering an incident end or an emission end for an optical signal of the optical transmission line; a collimator lens provided in the outer frame and facing the incident end or the emission end; and a support mechanism that is disposed in the outer frame and that maintains a posture of the collimator lens in the outer frame, a positioning surface that abuts on the collimator lens to maintain the posture of the collimator lens in the outer frame is provided in the outer frame, and the support mechanism includes: a biasing member; and a pressing member that presses the biasing member and biases the collimator lens toward the positioning surface with the biasing member.

Advantageous Effects of Invention

According to an optical connector and a medical device of the present disclosure, the posture of a collimator lens can be favorably maintained, and the reliability of optical communication can be secured.

BRIEF DESCRIPTION OF DRAWINGS

FIG. 6 illustrates a configuration of a plug according to a second embodiment.
FIG. 11 illustrates the configuration of the plug according to the fourth embodiment.

DESCRIPTION OF EMBODIMENTS

Figure 1:
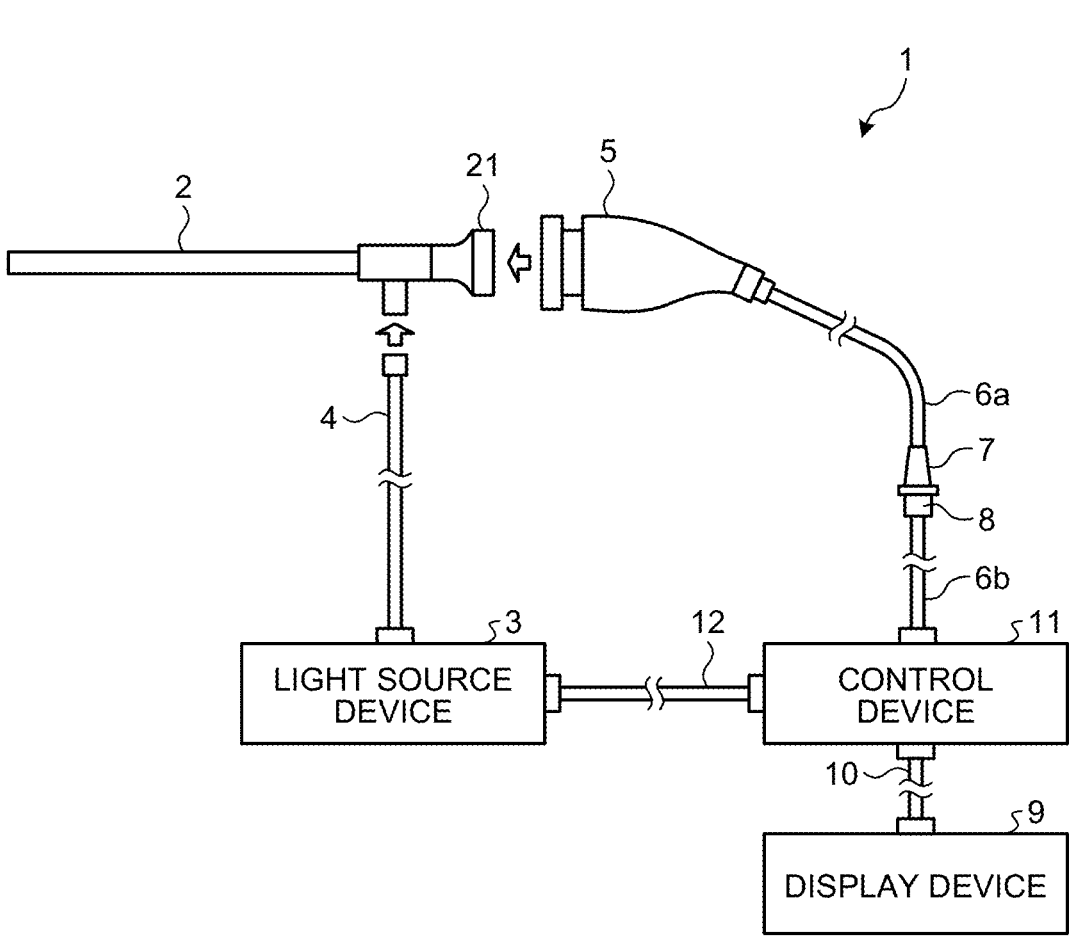
FIG. 1 illustrates a configuration of a medical observation system according to a first embodiment.

Embodiments for carrying out the present disclosure (hereinafter, embodiments) will be described below with reference to the drawings. Note that the present disclosure is not limited by the embodiments described below. Moreover, in the drawings, the same reference signs are given to the same parts.

[Schematic Configuration of Medical Observation System]

FIG. 1 illustrates a configuration of a medical observation system 1 according to a first embodiment.

The medical observation system 1 is used in the medical field for observing a subject (inside of living body in first embodiment). Then, the medical observation system 1 corresponds to a medical device according to the present disclosure. As illustrated in FIG. 1, the medical observation system 1 includes an insertion portion 2, a light source device 3, a light guide 4, a camera head 5, first and second transmission cables 6a and 6b, a plug 7, a receptacle 8, a display device 9, a third transmission cable 10, a control device 11, and a fourth transmission cable 12.

In the first embodiment, the insertion portion 2 includes a rigid endoscope. That is, the insertion portion 2 has an elongated shape. The insertion portion 2 is entirely hard, or has a soft part and the other hard part. The insertion portion 2 is inserted into a living body. An optical system (not illustrated) is provided in the insertion portion 2. The optical system includes one or a plurality of lenses, and collects light from a subject.

One end of the light guide 4 is connected to the light source device 3. The light source device 3 supplies light for illuminating the inside of a living body to one end of the light guide 4 under the control of the control device 11.

Note that, although the light source device 3 is configured separately from the control device 11 in the first embodiment, this is not a limitation. A configuration in which the light source device 3 is provided inside the control device 11 may be adopted.

One end of the light guide 4 is detachably connected to the light source device 3, and the other end thereof is detachably connected to the insertion portion 2. Then, the light guide 4 transmits light supplied from the light source device 3 from one end to the other end, and supplies the light to the insertion portion 2. The light (subject image) applied to the inside of the living body and reflected in the living body is collected by an optical system (not illustrated) in the insertion portion 2.

The camera head 5 corresponds to a medical observation device according to the present disclosure. The camera head 5 is detachably connected to a proximal end (eyepiece portion 21 (FIG. 1)) of the insertion portion 2. Furthermore, the camera head 5 includes an imaging element (not illustrated) and an electrooptical conversion element (not illustrated). The imaging element captures a subject image. The electrooptical conversion element electrooptically converts a captured image (electric signal) obtained by imaging of the imaging element into an optical signal. Then, under the control of the control device 11, the camera head 5 captures a subject image whose light has been collected at the insertion portion 2, photoelectrically converts the captured image (electric signal) obtained by the capturing into an optical signal, and outputs the optical signal.

The first transmission cable 6a is a composite cable in which an optical fiber 6a1 (see FIGS. 2 and 3) and an electric signal cable (not illustrated) are disposed inside an outer sheath (not illustrated), which is an outermost layer. The optical fiber 6a1 is an optical transmission line that transmits the optical signal (captured image) output from the camera head 5. Then, one end of the first transmission cable 6a is connected to the camera head 5.

Similarly to the first transmission cable 6a, the second transmission cable 6b is a composite cable in which an optical fiber 6b1 (see FIGS. 4 and 5) and an electric signal cable (not illustrated) are disposed inside an outer sheath (not illustrated), which is an outermost layer. Then, one end of the second transmission cable 6b is connected to the control device 11.

The above-described first and second transmission cables 6a and 6b correspond to two transmission cables according to the present disclosure.

The plug 7 is a male connector, and corresponds to an optical connector according to the present disclosure. Then, the plug 7 is attached to the other end of the first transmission cable 6a.

The receptacle 8 is a female connector. Then, the receptacle 8 is attached to the other end of the second transmission cable 6b.

Connection of the plug 7 and the receptacle 8 as described above with each other causes the first and second transmission cables 6a and 6b to be electrically and optically connected, and enables transmission of an electric signal and an optical signal. This causes the first and second transmission cables 6a and 6b to transmit the optical signal (captured image) output from the camera head 5 to the control device 11 and transmit a control signal, a synchronization signal, a clock, electric power, and the like output from the control device 11 to the camera head 5.

Note that a detailed structure of the plug 7 will be described in "Configuration of Plug" to be described later.

The display device 9 includes a display formed of, for example, liquid crystal or organic electro luminescence (EL). The display device 9 displays an image based on a video signal from the control device 11 under the control of the control device 11.

One end of the third transmission cable 10 is detachably connected to the display device 9, and the other end thereof is detachably connected to the control device 11. Then, the third transmission cable 10 transmits the video signal that has been processed by the control device 11 to the display device 9.

The control device 11 includes a central processing unit (CPU) and a field-programmable gate array (FPGA), and comprehensively controls the operations of the light source device 3, the camera head 5, and the display device 9.

Specifically, the control device 11 acquires the optical signal (captured image) output from the camera head 5 via the first and second transmission cables 6a and 6b, and photoelectrically converts the optical signal into an electric signal. Then, the control device 11 performs various types of image processing on the photoelectrically converted electric signal (captured image), and causes the display device 9 to display the captured image subjected to the image processing. Furthermore, the control device 11 outputs a control signal and the like to the camera head 5 via the first and second transmission cables 6a and 6b. Moreover, the control device 11 outputs a control signal and the like to the light source device 3 via the fourth transmission cable 12, and executes dimming control and the like.

One end of the fourth transmission cable 12 is detachably connected to the light source device 3, and the other end thereof is detachably connected to the control device 11. Then, the fourth transmission cable 12 transmits a control signal from the control device 11 to the light source device 3.

[Configuration of Plug]

Next, the configuration of the plug 7 will be described. Note that a "distal end side" used below when the configuration of the plug 7 is described means a side of the receptacle 8 (right side in FIG. 2) connected to the plug 7, and a "proximal end side" used below means a side away from the receptacle 8 (side of camera head 5, left side in FIG. 2).

Figure 2:
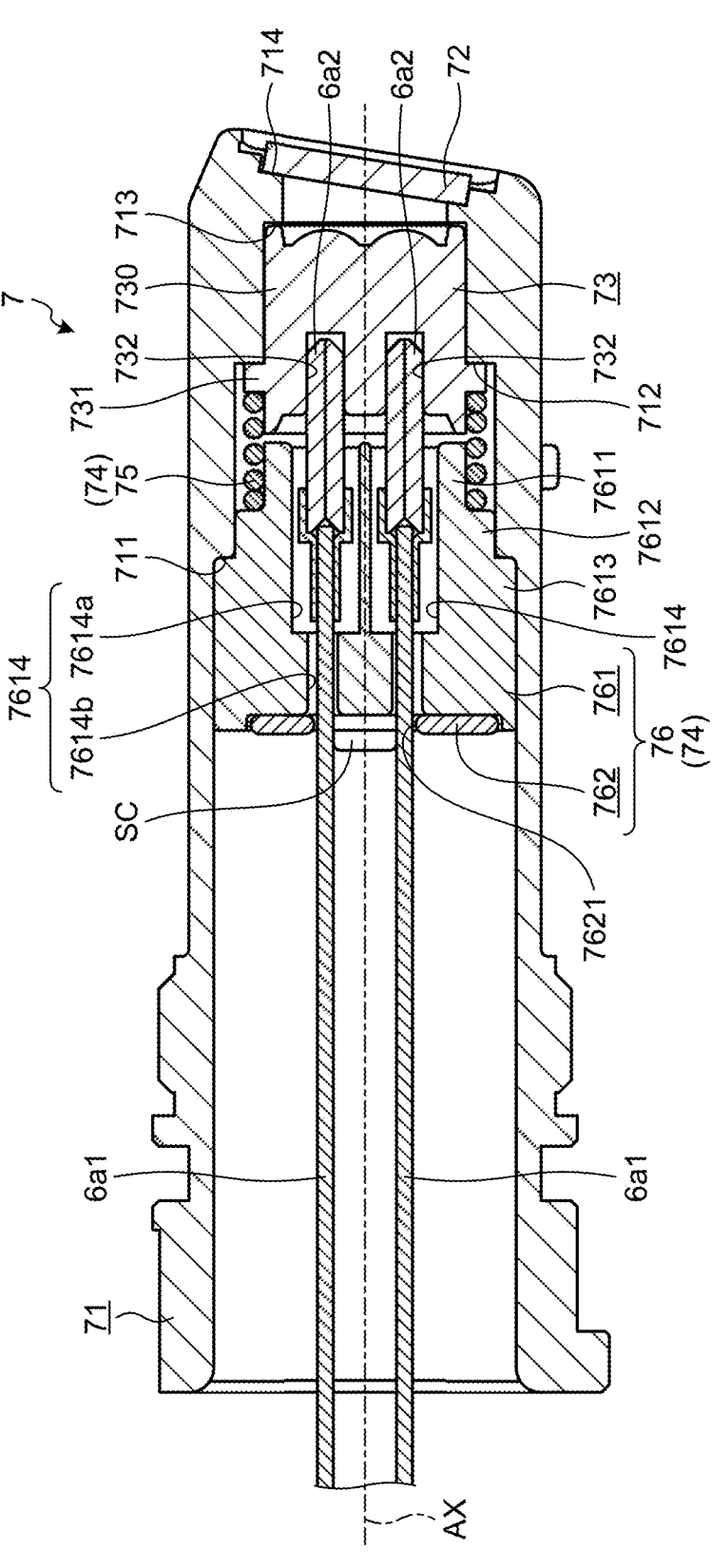
FIG. 2 illustrates a configuration of a plug.
Figure 3:
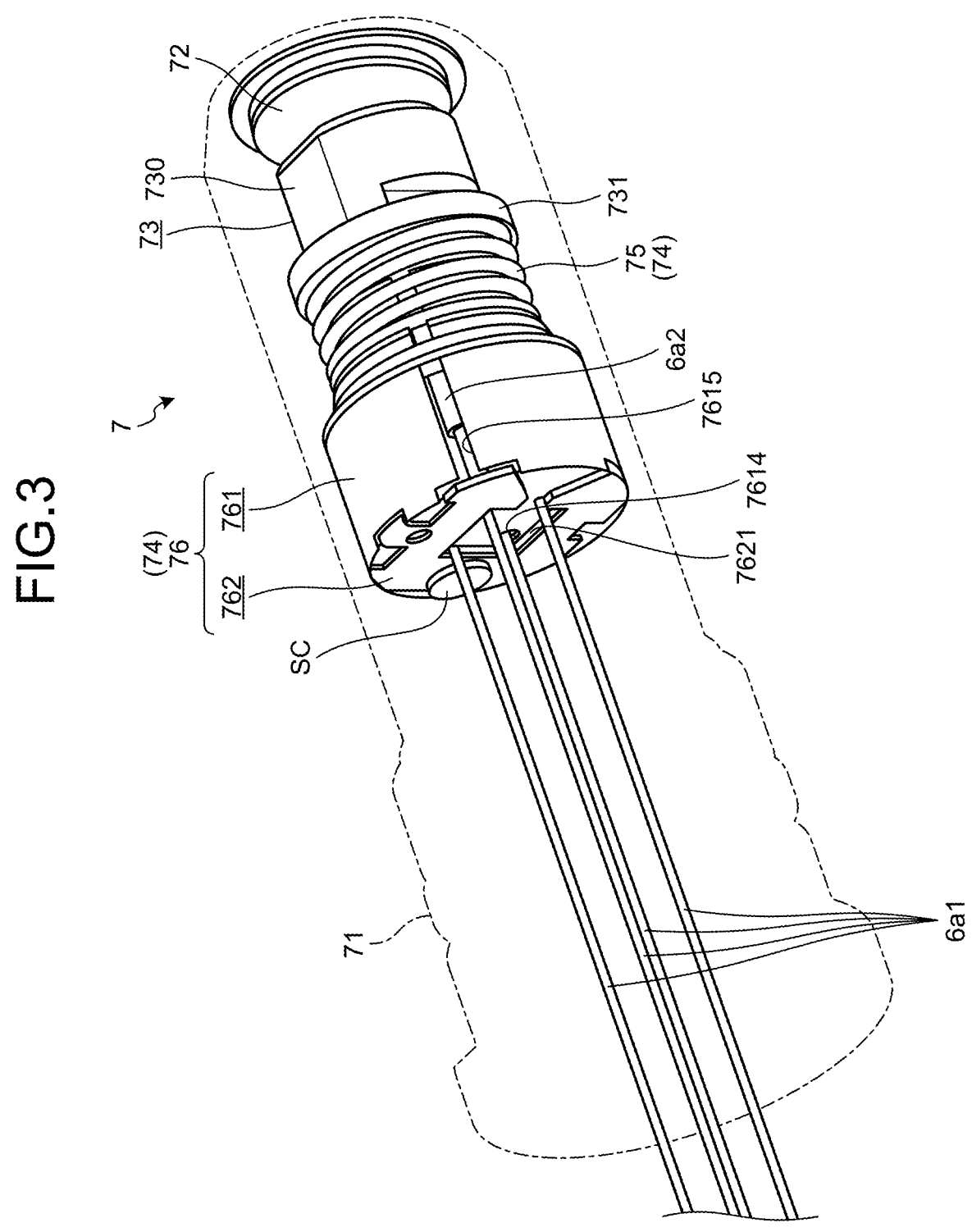
FIG. 3 illustrates the configuration of the plug.

FIGS. 2 and 3 illustrate the configuration of the plug 7. Specifically, FIG. 2 is a cross-sectional view of the plug 7 taken along a plane passing through a central axis Ax of an outer frame 71. FIG. 3 is a perspective view of the plug 7 as viewed from the proximal end side.

Note that, for convenience of description, only a portion of the plug 7 optically connected to the receptacle 8 will be described below. FIGS. 2 and 3 also illustrate only the portion. Furthermore, for convenience of description, FIG. 3 illustrates the outer frame 71 with a dot-dashed line.

As illustrated in FIG. 2 or 3, the plug 7 includes the outer frame 71, a cover member 72, a collimator lens 73, and a support mechanism 74.

The outer frame 71 is made of a metal material, and has a substantially circular cylindrical shape as illustrated in FIG. 2 or 3. Note that the shape of the outer frame 71 is not limited to the circular cylindrical shape as long as the outer frame 71 has a cylindrical shape. The outer frame 71 may have a cylinder having another cross-sectional shape. Then, the optical fiber 6a1 constituting the first transmission cable 6a is inserted into the outer frame 71 along the central axis Ax. This causes the outer frame 71 to cover an emission end for an optical signal of the optical fiber 6a1.

Here, in the first embodiment, four optical fibers 6a1 constituting the first transmission cable 6a are provided as illustrated in FIG. 3. Then, as illustrated in FIG. 2, each ferrule 6a2 is provided at an emission end for an optical signal of each of the optical fibers 6al.

The outer frame 71 has an inner surface having three steps from the proximal end side toward the distal end side and having an inner diameter dimension decreasing stepwise. For convenience of description, a step located closest to the proximal end side among the three steps is referred to as a first positioning surface 711 (FIG. 2). A step located second closest to the proximal end side is referred to as a second positioning surface 712 (FIG. 2). A step located closest to the distal end side is referred to as a third positioning surface 713 (FIG. 2).

As illustrated in FIG. 2, the first positioning surface 711 is an annular flat surface facing the proximal end side, and is located in a plane substantially orthogonal to the central axis Ax. Then, the first positioning surface 711 abuts on a pressing member 76 constituting the support mechanism 74 to position the pressing member 76 in the outer frame 71 in a direction along the central axis Ax.

The second positioning surface 712 corresponds to a positioning surface according to the present disclosure. As illustrated in FIG. 2, similarly to the first positioning surface 711, the second positioning surface 712 is an annular flat surface facing the proximal end side, and is located in a plane substantially orthogonal to the central axis Ax. Then, the second positioning surface 712 abuts on the collimator lens 73 to maintain the posture of the collimator lens 73 in the outer frame 71.

As illustrated in FIG. 2, similarly to the first positioning surface 711, the third positioning surface 713 is an annular flat surface facing the proximal end side, and is located in a plane substantially orthogonal to the central axis Ax. In the first embodiment, the third positioning surface 713 has predetermined clearance between the third positioning surface 713 and the collimator lens 73 in a state in which the collimator lens 73 abuts on the second positioning surface 712.

Furthermore, as illustrated in FIG. 2, an attachment portion 714 for attaching the cover member 72 is provided on an inner peripheral edge of the distal end of the outer frame 71.

Specifically, as illustrated in FIG. 2, the attachment portion 714 is a recess recessed in a direction inclined at a predetermined angle with respect to the central axis Ax. A bottom portion of the attachment portion 714 is configured by an annular flat surface.

The cover member 72 includes flat plates whose plate surfaces on both sides are parallel to each other. Then, the cover member 72 is applied to the bottom portion of the attachment portion 714, and is airtightly connected to the outer frame 71 (attachment portion 714) by soldering, brazing, bonding, or glass sealing.

Each plate surface of the cover member 72 is inclined at a predetermined angle with respect to a plane orthogonal to the central axis Ax by being joined as described above.

The above-described cover member 72 is made of glass, sapphire single crystal having resistance to heat and chemicals, or the like.

Note that an antireflection film may be provided on at least one of the plate surfaces of the cover member 72.

As illustrated in FIG. 2, the collimator lens 73 has a substantially columnar shape, and is disposed in the outer frame 71 in a state in which a lens optical axis Bx' (central axis of each optical path of lens, see FIGS. 4 and 5) of the collimator lens 73 substantially coincides with the direction along the central axis Ax. In the state of being disposed in the outer frame 71, the collimator lens 73 is located on the proximal end side of the cover member 72, and faces the emission end (ferrule 6a2) of the optical fiber 6a1. Then, the collimator lens 73 collimates light (optical signal) emitted from the emission end of the optical fiber 6a1. In the first embodiment, the collimator lens 73 is a resin lens made of a resin material such as polyetherimide resin. Furthermore, the collimator lens 73 is a single lens facing the emission ends of the four optical fibers 6a1, and collimates light emitted from the emission ends.

As illustrated in FIG. 2 or 3, an annular projecting portion 731 is provided on the outer peripheral surface of the collimator lens 73. The projecting portion 731 projects in a direction away from the lens optical axis Bx' of the collimator lens 73.

An end surface of the projecting portion 731 on the distal end side is a flat surface, and is located in a plane orthogonal to the lens optical axis Bx' of the collimator lens 73.

Note that, in the following description, for convenience of description, a columnar portion other than the projecting portion 731 of the collimator lens 73 is referred to as a lens body 730.

In the first embodiment, the outer diameter dimension of the annular projecting portion 731 is slightly smaller than the outer diameter dimension of the annular second positioning surface 712. Furthermore, the outer diameter dimension of the lens body 730 is slightly smaller than the inner diameter dimension of the second positioning surface 712 (outer diameter dimension of the third positioning surface 713). That is, the collimator lens 73 is disposed in a state of having predetermined clearance between the collimator lens 73 and the inner surface of the outer frame 71 in a radial direction centered on the central axis Ax.

Furthermore, as illustrated in FIG. 2, a recess 732 is provided on an end surface on the proximal end side of the lens body 730. The recess 732 extends toward the distal end side. The emission end (ferrule 6a2) of the optical fiber 6a1 is inserted into the recess 732.

In the first embodiment, since four optical fibers 6a1 are provided, four recesses 732 are also provided.

The support mechanism 74 is provided in the outer frame 71, and maintains the posture of the collimator lens 73 in the outer frame 71. As illustrated in FIG. 2 or 3, the support mechanism 74 includes a biasing member 75 and the pressing member 76.

In the first embodiment, the biasing member 75 includes a coil spring. Note that the biasing member 75 is not limited to the coil spring, and may be configured by another biasing member including an elastic member having elasticity such as a plate spring and rubber. Then, the biasing member 75 is disposed in a state in which a portion closer to the proximal end side than the projecting portion 731 of the lens body 730 is inserted into the inside. In this state, one end (end on distal end side) of the biasing member 75 abuts on the end surface of the projecting portion 731 on the proximal end side.

The pressing member 76 presses the biasing member 75, and the biases the collimator lens 73 toward the second positioning surface 712 with the biasing member 75. The biasing causes the support mechanism 74 to bring the end surface of the projecting portion 731 on the distal end side into contact with the second positioning surface 712 and maintain the posture of the collimator lens 73 in the outer frame 71. That is, in the collimator lens 73, the end surface of the projecting portion 731 on the distal end side abuts on the second positioning surface 712, so that the position of the collimator lens 73 in the direction along the central axis Ax is maintained, and the state in which the lens optical axis Bx' of the collimator lens 73 is substantially parallel to the central axis Ax is maintained.

Furthermore, in order to prevent moisture from entering an area serving as an optical path from the outside of the outer frame 71, a resin of a slow curing type or a thermal curing type is injected to the outside of the pressing member 76 to perform sealing.

Then, as illustrated in FIG. 2 or 3, the pressing member 76 includes a pressing member body 761 and a prevention member 762 that prevents inflow of the injected resin.

The pressing member body 761 is a portion that presses the biasing member 75, has a substantially columnar shape, and is disposed in a posture in which the central axis of the column substantially coincides with the central axis Ax. As illustrated in FIG. 2 or 3, the pressing member body 761 includes a small diameter portion 7611, a pressing portion 7612, and a large diameter portion 7613.

The small diameter portion 7611 is provided at an end of the pressing member body 761 on the distal end side, and has a columnar shape having an outer diameter dimension substantially the same as the outer diameter dimension of the lens body 730. Then, as illustrated in FIG. 2, the small diameter portion 7611 is disposed in a state of being inserted into the biasing member 75.

The pressing portion 7612 has a columnar shape having an outer diameter dimension larger than the outer diameter dimension of the small diameter portion 7611, and is integrally formed in a state of being coaxial with an end of the small diameter portion 7611 on the proximal end side. Then, the pressing portion 7612 abuts on the other end (end on proximal end side) of the biasing member 75 at the end surface on the distal end side, and presses the biasing member 75 toward the distal end side.

The large diameter portion 7613 has a columnar shape having an outer diameter dimension larger than the outer diameter dimension of the pressing portion 7612, and is integrally formed in a state of being coaxial with an end of the pressing portion 7612 on the proximal end side.

In the first embodiment, the outer diameter dimensions of the pressing portion 7612 and the large diameter portion 7613 of the pressing member body 761 are set to be slightly larger than the inner diameter dimensions at corresponding positions of the outer frame 71. Then, the pressing member body 761 is press-fitted into the outer frame 71 in a state in which the end surface of the large diameter portion 7613 on the distal end side abuts on the first positioning surface 711. That is, the pressing member body 761 (pressing member 76) is fixed in the outer frame 71.

Furthermore, as illustrated in FIG. 2 or 3, a storage hole 7614 (FIG. 2) and an installation hole 7615 (FIG. 3) are provided in the pressing member body 761.

As illustrated in FIG. 2, the storage hole 7614 penetrates from the end surface on the distal end side to the end surface on the proximal end side of the pressing member body 761. Then, a portion of the optical fiber 6a1 on the emission end (ferrule 6a2) side is stored in the storage hole 7614. The storage hole 7614 has a large diameter hole 7614a and a small diameter hole 7614b. The large diameter hole 7614a is located on the distal end side. The small diameter hole 7614b is located on the proximal end side, and communicates with the large diameter hole 7614a. The storage hole 7614 has an inner surface formed stepwise.

The large diameter hole 7614a has an inner diameter dimension slightly larger than the outer diameter dimension of the ferrule 6a2.

The small diameter hole 7614b has an inner diameter dimension smaller than the inner diameter dimension of the large diameter hole 7614a and slightly larger than the outer diameter dimension of the optical fiber 6a1.

In the first embodiment, since four optical fibers 6a1 are provided, four storage holes 7614 are provided.

As illustrated in FIG. 3, the installation hole 7615 penetrates from the outer peripheral surface of the pressing member body 761 into the storage hole 7614. Then, the installation hole 7615 is used when the portion of the optical fiber 6a1 on the emission end (ferrule 6a2) side is stored in the storage hole 7614. That is, the portion of the optical fiber 6a1 on the emission end (ferrule 6a2) side is stored in the storage hole 7614 from the outer peripheral surface of the pressing member body 761 via the installation hole 7615.

In the first embodiment, since four optical fibers 6a1 are provided, four installation holes 7615 are provided in correspondence with storage holes 7614.

The prevention member 762 includes a plate body having a cutout 7621 (FIGS. 2 and 3) that surrounds all the storage holes 7614 as viewed from the proximal end side. Then, the prevention member 762 is fixed to the end surface of the pressing member body 761 on the proximal end side by a fixing member SC (FIGS. 2 and 3) such as a screw in a state in which all the optical fibers 6a1 are located in the cutout 7621. This causes the prevention member 762 to prevent injected resin from flowing into the biasing member 75, the ferrule 6a2, and the recess 732 of a collimator lens 73B via the installation hole 7615.

According to the above-described first embodiment, the following effects are exhibited.

Figure 4:
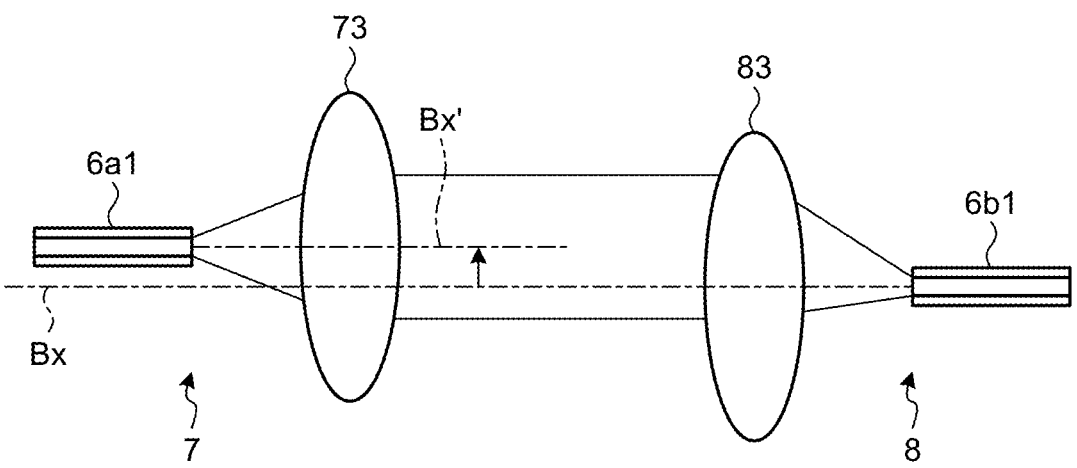
FIG. 4 illustrates effects of the first embodiment.
Figure 5:
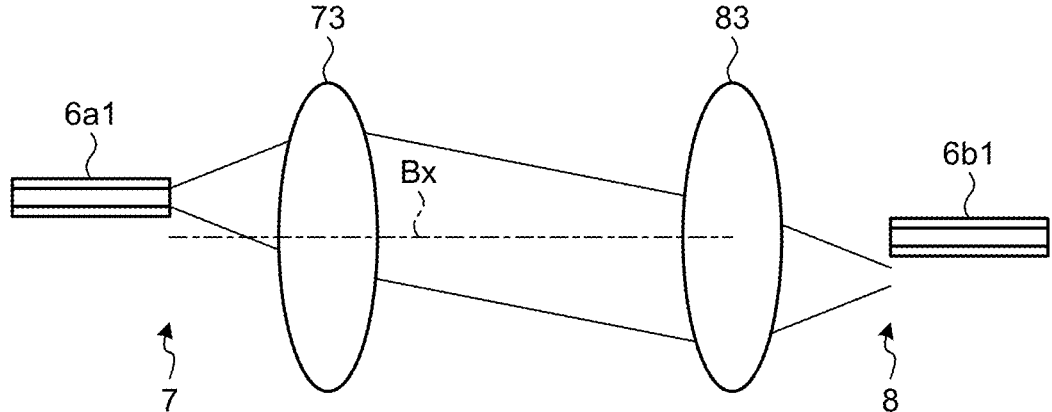
FIG. 5 illustrates the effects of the first embodiment.

FIGS. 4 and 5 illustrate the effects of the first embodiment. Specifically, FIG. 4 illustrates a case where the lens optical axis Bx' of the collimator lens 73 is shifted with respect to a lens optical axis Bx of a collimator lens 83 constituting the receptacle 8 in the radial direction centered on the central axis Ax. FIG. 5 illustrates a case where the lens optical axis Bx' of the collimator lens 73 is inclined with respect to the lens optical axis Bx of the collimator lens 83.

In the plug 7 according to the first embodiment, the collimator lens 73 is made of a resin material. This enables manufacturing of the collimator lens 73 at lower cost than that in a case where the collimator lens 73 is made of glass and the like.

By the way, when the collimator lens 73 is made of a resin material, there is a difference in a linear expansion coefficient between the collimator lens 73 and the outer frame 71 made of a metal material. That is, unnecessary stress is applied to the collimator lens 73 due to a difference in volume fluctuation between the collimator lens 73 and the outer frame 71, which may deform the collimator lens 73 or change the posture thereof.

In the first embodiment, the collimator lens 73 is disposed in a state of having predetermined clearance between the collimator lens 73 and the inner surface of the outer frame 71 in a radial direction centered on the central axis Ax. Furthermore, the collimator lens 73 is disposed in a state of being biased by the biasing member 75 and abutting on the second positioning surface 712. This prevents the unnecessary stress from being applied to the collimator lens 73 due to the difference in volume fluctuation between the collimator lens 73 and the outer frame 71, and prevents deformation of the collimator lens 73.

Here, a case is assumed in which the collimator lens 73 moves in a radial direction centered on the central axis Ax due to the difference in volume fluctuation between the collimator lens 73 and the outer frame 71, that is, the lens optical axis Bx' of the collimator lens 73 is shifted with respect to the lens optical axis Bx while being in parallel to the lens optical axis Bx of the collimator lens 83 (hereinafter, referred to as first case).

In the first case, as illustrated in FIG. 4, collimated light emitted from the collimator lens 73 is maintained to be parallel to the lens optical axes Bx and Bx'. This maintains a point of light emitted from the plug 7 (collimator lens 73) and collected via the collimator lens 83 at a position of an incident end of the optical fiber 6*b*1. That is, in the first case, no problem occurs.

In contrast, for example, a case is assumed in which the lens optical axis Bx' of the collimator lens 73 is inclined with respect to the lens optical axis Bx of the collimator lens 83 (hereinafter, referred to as second case).

In the second case, as illustrated in FIG. 5, collimated light emitted from the collimator lens 73 is not maintained to be parallel to the lens optical axes Bx and Bx'. This causes the point of light emitted from the plug 7 (collimator lens 73) and collected via the collimator lens 83 constituting the receptacle 8 to deviate from the incident end of the optical fiber 6*b*1. That is, in the case, reliability of optical communication cannot be secured.

In the first embodiment, the collimator lens 73 is disposed in a state of being biased by the biasing member 75 and abutting on the second positioning surface 712. This maintains the position of the collimator lens 73 in the direction along the central axis Ax, and maintains the state in which the lens optical axis Bx' of the collimator lens 73 is substantially parallel to the central axis Ax (state in which lens optical axis Bx' substantially coincides with lens optical axis Bx of the collimator lens 83). That is, a structure in which the second case does not occur is provided.

Therefore, according to the plug 7 of the first embodiment, the posture of the collimator lens 73 can be favorably maintained, and the reliability of optical communication can be secured.

Furthermore, in the first embodiment, the collimator lens 73 is a single lens facing the emission ends of the four optical fibers 6*a*1, and collimates light emitted from the emission ends. This facilitates positioning of each optical fiber 6*a*1 and the collimator lens 73 and manufacturing of the plug 7 as compared to a configuration in which collimator lenses are provided for the four optical fibers 6*a*1.

Second Embodiment

Next, a second embodiment will be described.

In the following description, the same reference signs are attached to configurations similar to those in the above-described first embodiment, and detailed description thereof will be omitted or simplified.

In the second embodiment, the configuration of the plug 7 is changed from that of the above-described first embodiment. For convenience of description, the plug 7 according to the second embodiment will be hereinafter referred to as a plug 7A.

Figure 6:
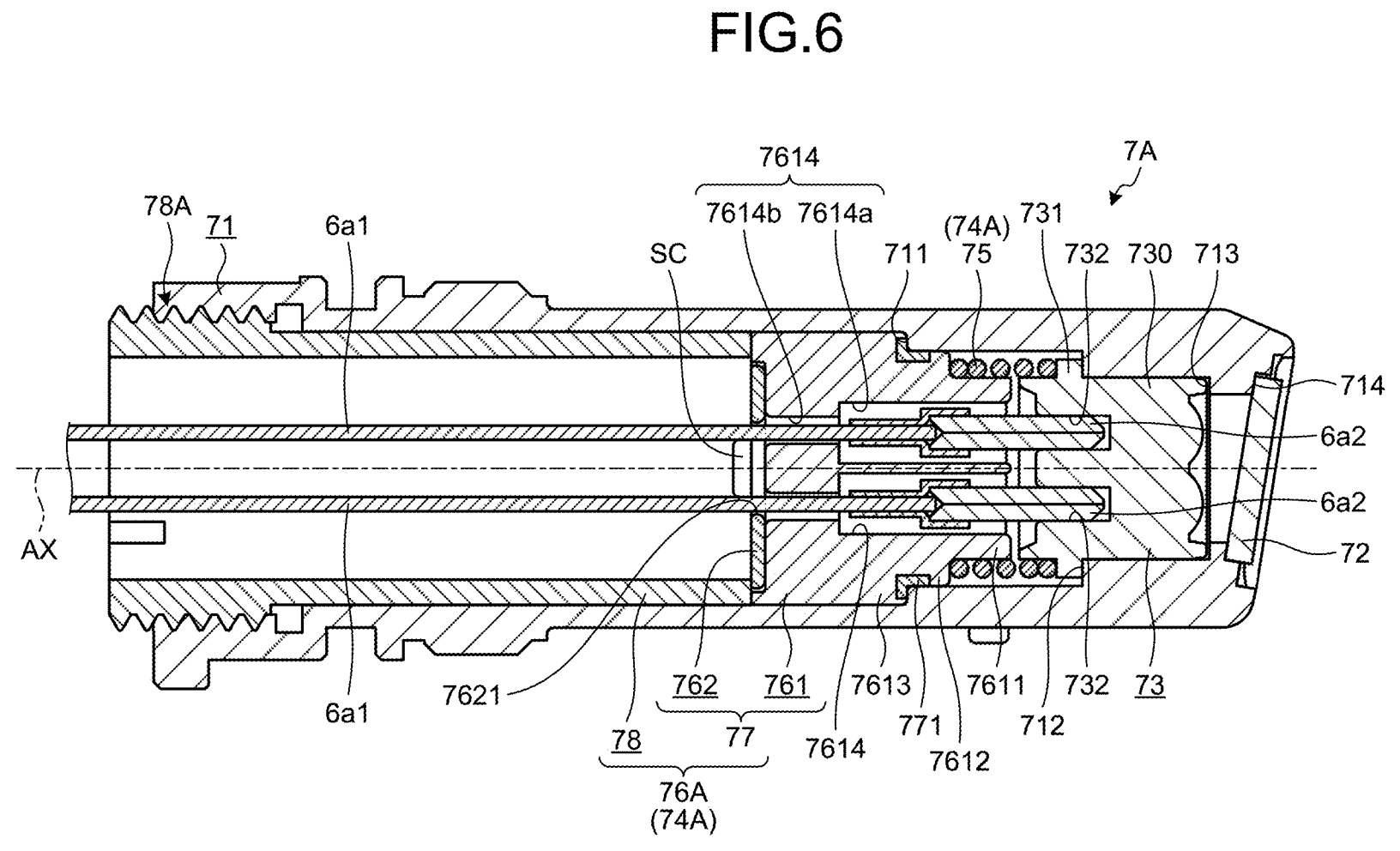
Figure 7:
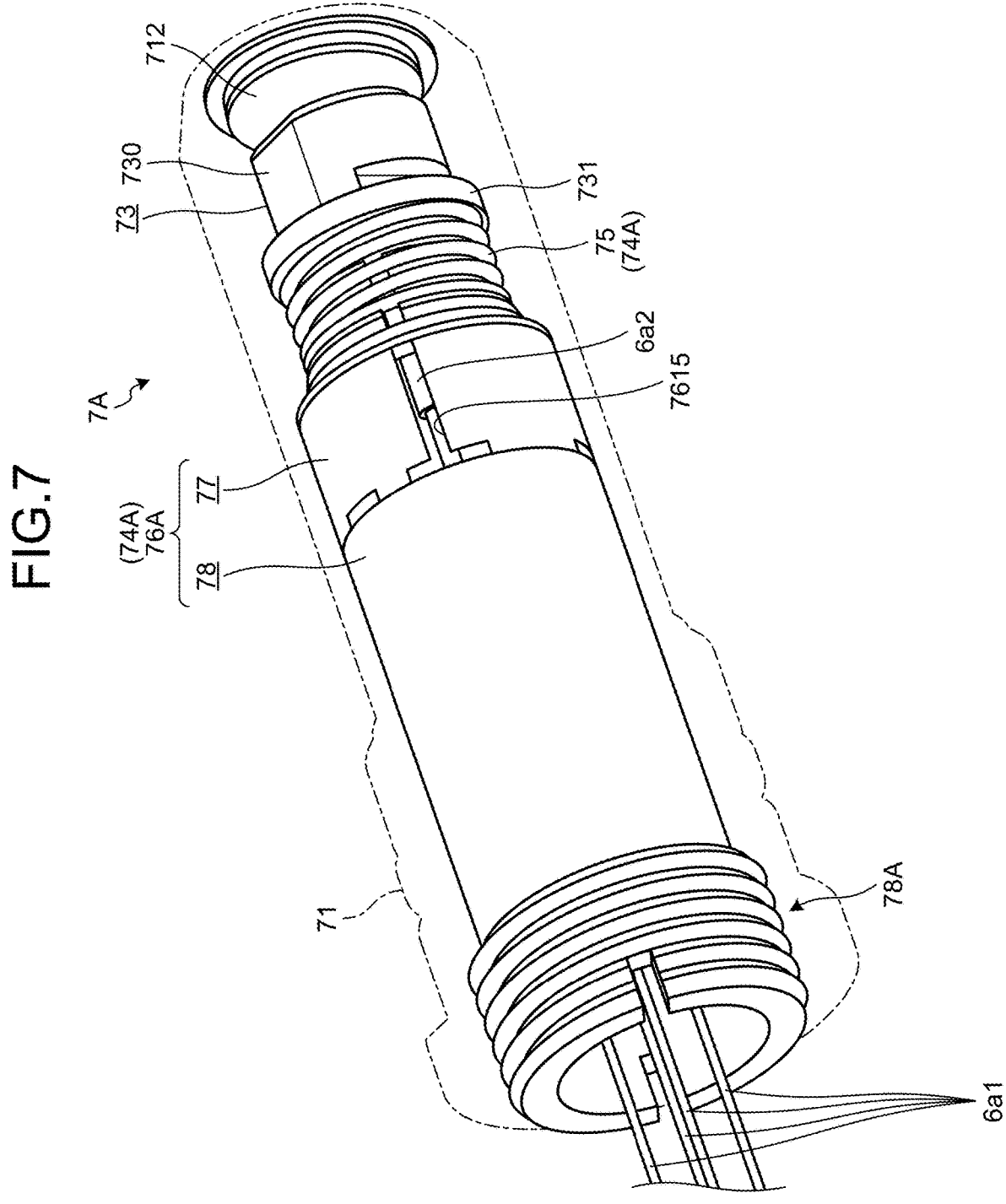
FIG. 7 illustrates the configuration of the plug according to the second embodiment.

FIGS. 6 and 7 illustrate a configuration of the plug 7A according to the second embodiment. Specifically, FIG. 6 corresponds to FIG. 2. FIG. 7 corresponds to FIG. 3.

In the plug 7A, as illustrated in FIG. 6 or 7, the configuration of the pressing member 76 of the support mechanism 74 is changed from that of the plug 7 described in the above-described first embodiment. For convenience of description, the support mechanism 74 and the pressing member 76 according to the second embodiment will be hereinafter referred to as a support mechanism 74A and a pressing member 76A, respectively.

As illustrated in FIG. 6 or 7, the pressing member 76A includes a pressing member body 77 and a regulating member 78.

The pressing member body 77 has a configuration similar to that of the pressing member 76 described in the above-described first embodiment. Note that, in the pressing member body 77, the same reference signs are attached to configurations similar to those of the pressing member 76.

Here, unlike the pressing member 76, the outer diameter dimensions of the pressing portion 7612 and the large diameter portion 7613 of the pressing member body 77 are set to be slightly smaller than the inner diameter dimensions at corresponding positions of the outer frame 71. The pressing member body 77 can move along the central axis Ax in the outer frame 71.

Furthermore, in the pressing member body 77, a sealing material 771 is provided at a corner portion between the end surface of the large diameter portion 7613 on the distal end side and the outer peripheral surface of the pressing portion 7612 as illustrated in FIGS. 6 and 7.

The sealing material 771 is an O-ring or an adhesive member such as a silicone resin and an epoxy resin, and is sandwiched between the above-described corner portion of the pressing member body 77 and the first positioning surface 711 to prevent liquid entry.

The regulating member 78 is configured detachably from the outer frame 71, and regulates movement toward a direction (proximal end side) opposite to a biasing direction of the collimator lens 73 caused by the biasing member 75 in the pressing member body 77. In the second embodiment, the regulating member 78 has a shape of a circular cylinder into which the optical fiber 6*a*1 is inserted from the proximal end side of the outer frame 71 into the outer frame 71. Then, as illustrated in FIG. 6 or 7, screwing structures 78*a* screwed to each other are provided on the outer peripheral surface of the regulating member 78 on the proximal end side and the inner surface of the outer frame 71 on the proximal end side. That is, the regulating member 78 is inserted into the outer frame 71, and screwed to the outer frame 71 by the screwing structures 78*a*, so that the regulating member 78 presses the pressing member body 77 until the sealing material 771 of the pressing member body 77 abuts on the first positioning surface 711 at the end surface on the distal end side.

According to the above-described second embodiment, the following effect is exhibited in addition to effects similar to those in the above-described first embodiment.

In the plug 7A according to the second embodiment, the pressing member 76A includes the pressing member body 77 and the regulating member 78 described above. Therefore, if the regulating member 78 is removed from the outer frame 71, the collimator lens 73 can be replaced with a new collimator lens 73. Therefore, convenience can be improved.

Third Embodiment

Next, a third embodiment will be described.

In the following description, the same reference signs are attached to configurations similar to those in the thereof will be omitted or simplified.

In the third embodiment, the configuration of the plug 7 is changed from that of the above-described first embodiment. For convenience of description, the plug 7 according to the third embodiment will be hereinafter referred to as a plug 7B.

Figure 8:
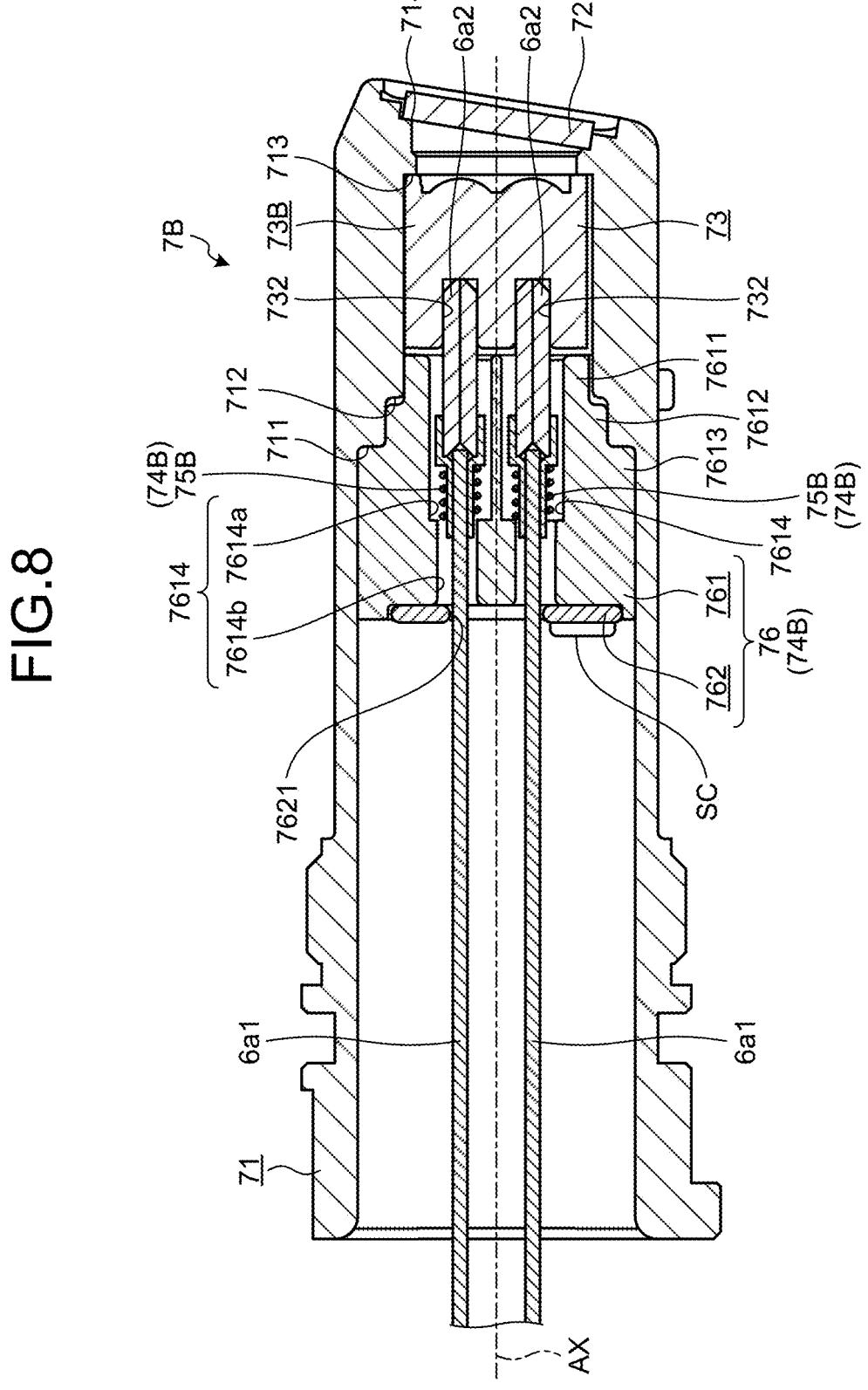
FIG. 8 illustrates a configuration of a plug according to a third embodiment.
Figure 9:
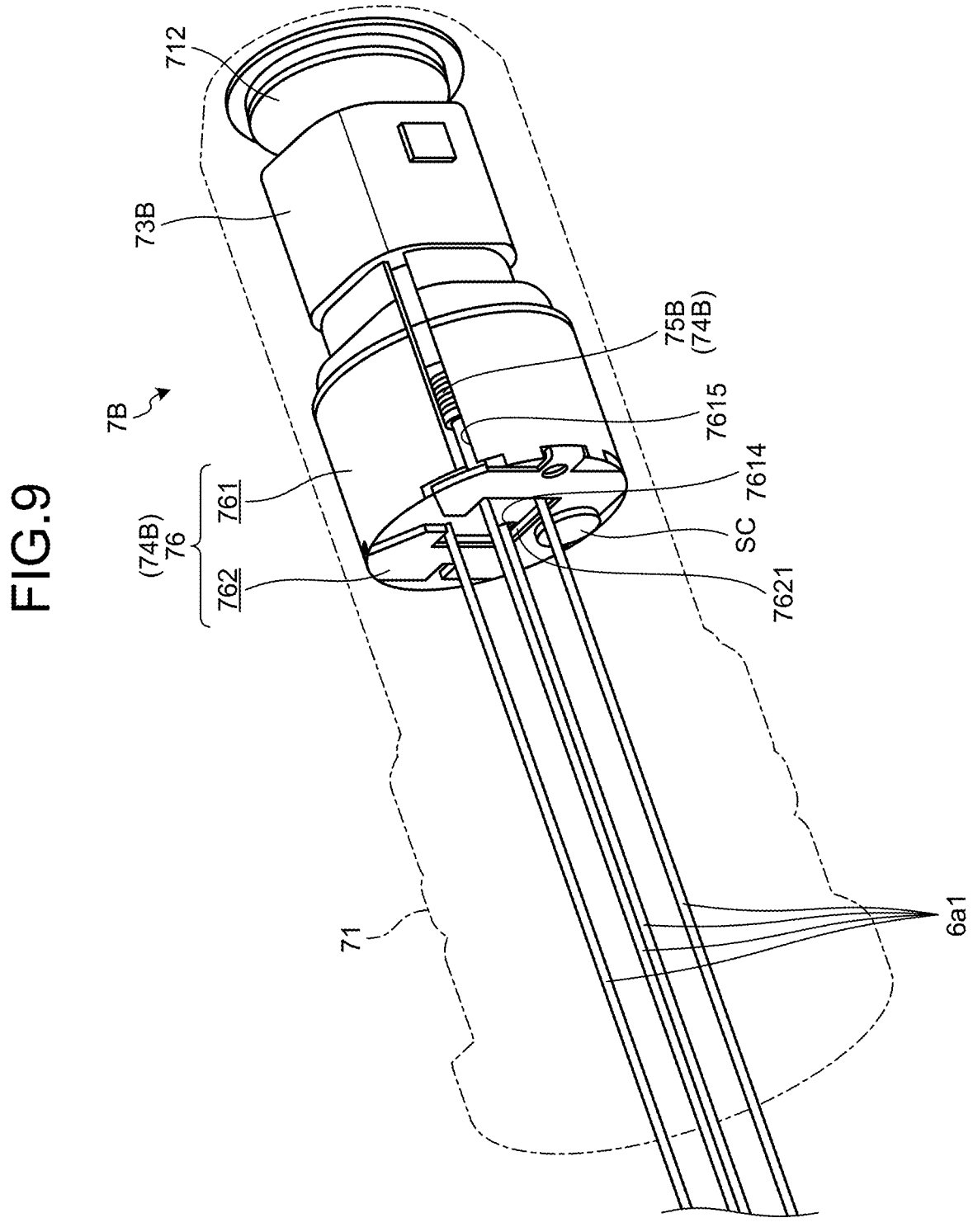
FIG. 9 illustrates the configuration of the plug according to the third embodiment.

FIGS. 8 and 9 illustrate a configuration of the plug 7B according to the third embodiment. Specifically, FIG. 8 corresponds to FIG. 2. FIG. 9 corresponds to FIG. 3.

In the plug 7B, as illustrated in FIG. 8 or 9, the configurations of the collimator lens 73 and the biasing member 75 of the support mechanism 74 are changed from that of the plug 7 described in the above-described first embodiment. For convenience of description, the collimator lens 73, the support mechanism 74, and the biasing member 75 according to the third embodiment will be hereinafter referred to as the collimator lens 73B, a support mechanism 74B, and a biasing member 75B, respectively.

The collimator lens 73B has a configuration in which the projecting portion 731 is omitted from the collimator lens 73 described in the above-described first embodiment, that is, a configuration similar to that of the lens body 730.

The biasing member 75B includes a coil spring similarly to the biasing member 75 described in the above-described first embodiment. Note that the biasing member 75B is not limited to the coil spring, and may be configured by another biasing member including an elastic member having elasticity such as a plate spring and rubber. As illustrated in FIG. 8 or 9, the biasing member 75B is disposed in the large diameter hole 7614*a* in a state where the optical fiber 6*a*1 is inserted into the biasing member 75B. In this state, one end (end on distal end side) of the biasing member 75B abuts on the ferrule 6*a*2, and the other end (end on proximal end side) abuts on the bottom surface of the large diameter hole 7614*a*. Then, the pressing member 76 is press-fitted into the outer frame 71, and pressed from the pressing member 76 (bottom surface of large diameter hole 7614*a*), so that the biasing member 75B biases the collimator lens 73B toward the third positioning surface 713 via the ferrule 6*a*2.

In the third embodiment, since four optical fibers 6*a*1 are provided, four biasing members 75B are provided.

The third positioning surface 713 according to the third embodiment corresponds to a positioning surface according to the present disclosure. That is, the collimator lens 73B is pressed toward the distal end side at the ferrule 6*a*2 by biasing of the biasing member 75B, and the end surface on the distal end side abuts on the third positioning surface 713.

Then, the end surface of the collimator lens 73B on the distal end side abuts on the third positioning surface 713, so that the position of the collimator lens 73B in the direction along the central axis Ax is maintained, and the state in which the lens optical axis of the collimator lens 73B substantially coincides with the central axis Ax is maintained.

Even when the plug 7B according to the above-described third embodiment is adopted, effects similar to those of the above-described first embodiment are exhibited.

Fourth Embodiment

Next, a fourth embodiment will be described.

In the following description, the same reference signs are attached to configurations similar to those in the thereof will be omitted or simplified.

In the fourth embodiment, the configuration of the plug 7 is changed from that of the above-described first embodiment. For convenience of description, the plug 7 according to the fourth embodiment will be hereinafter referred to as a plug 7C.

Figure 10:
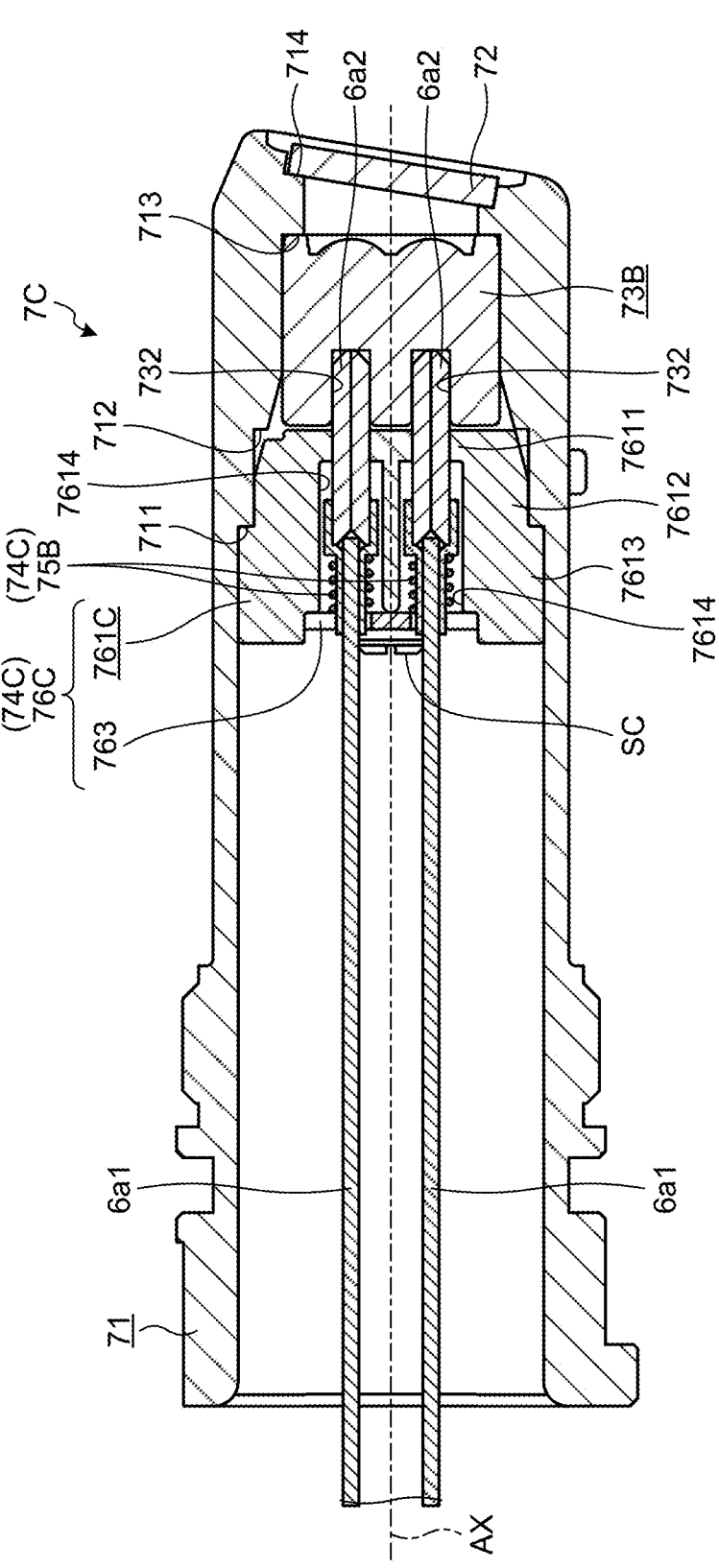
FIG. 10 illustrates a configuration of a plug according to a fourth embodiment.
Figure 11:
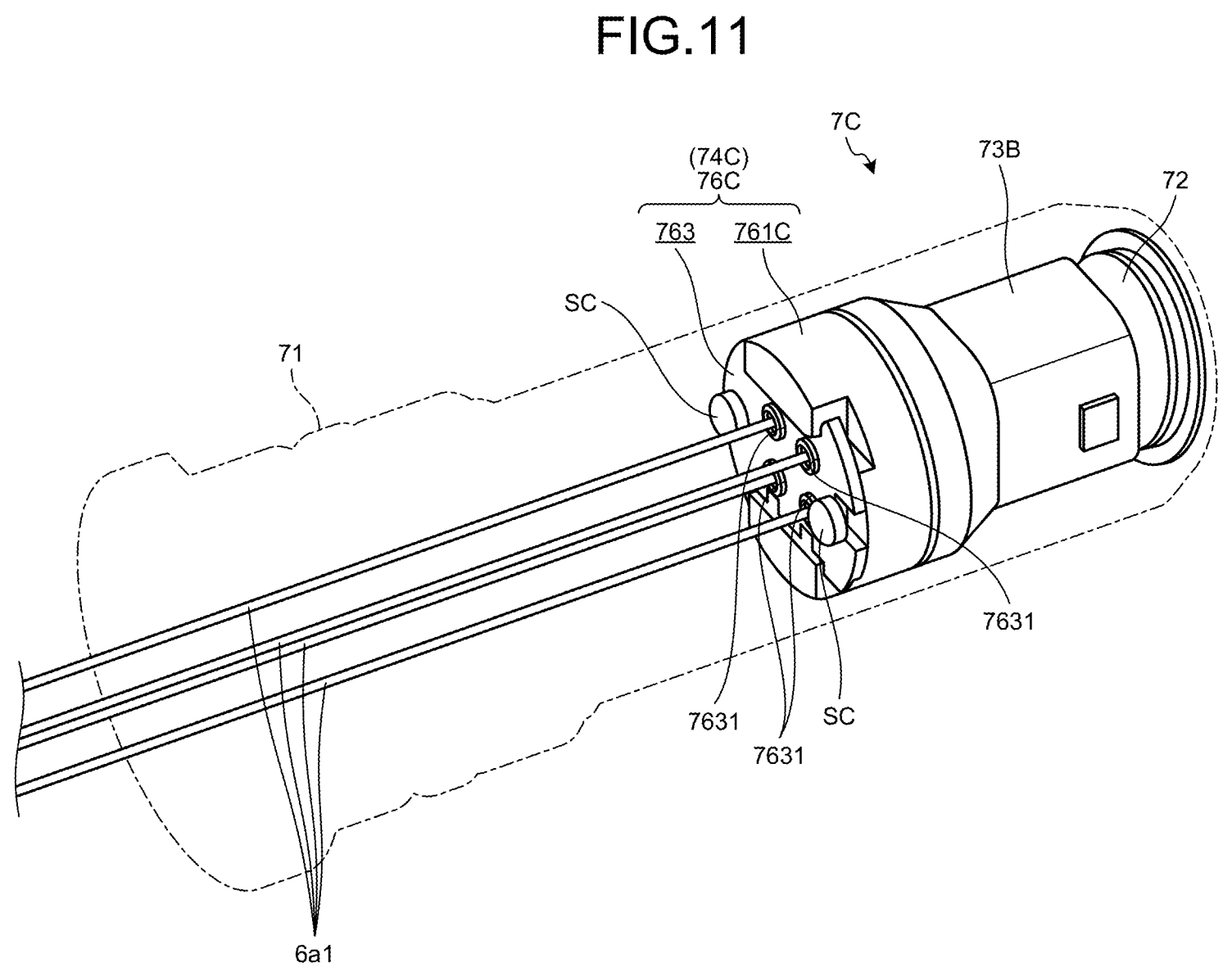

FIGS. 10 and 11 illustrate a configuration of the plug 7C according to the fourth embodiment. Specifically, FIG. 10 corresponds to FIG. 2. FIG. 11 corresponds to FIG. 3.

In the plug 7C, as illustrated in FIG. 10 or 11, the configurations of the collimator lens 73 and the support mechanism 74 are changed from that of the plug 7 described in the above-described first embodiment. Note that the collimator lens 73 according to the fourth embodiment is the same as the collimator lens 73B described in the third embodiment. For convenience of description, the support mechanism 74 according to the fourth embodiment will be hereinafter referred to as a support mechanism 74C.

In the support mechanism 74C, as illustrated in FIG. 10 or 11, the configuration of the biasing member 75 of the support mechanism 74 described in the above-described first embodiment is changed to the configuration of the biasing member 75B (FIG. 10) described in the above-described third embodiment, and the configuration of the pressing member 76 is changed. For convenience of description, the pressing member 76 according to the fourth embodiment will be hereinafter referred to as a pressing member 76C.

As illustrated in FIG. 10 or 11, the pressing member 76C includes a press-fit member 761C and a pressing member body 763.

The press-fit member 761C has a configuration substantially similar to that of the pressing member body 761 described in the above-described first embodiment. Note that, in the press-fit member 761C, the same reference signs are attached to configurations similar to those of the pressing member body 761.

Note that, as illustrated in FIG. 11, unlike the pressing member body 761 described in the above-described first embodiment, the press-fit member 761C has no installation hole 7615. Furthermore, as illustrated in FIG. 10, the storage hole 7614 of the press-fit member 761C has no small diameter hole 7614*b* described in the above-described first embodiment, and has a configuration in which the large diameter hole 7614*a* described in the above-described first embodiment extends to the end surface of the press-fit member 761C on the proximal end side. Moreover, the storage hole 7614 has an inner diameter dimension on the distal end side smaller than another inner diameter dimension, and is set to have a dimension slightly larger than the outer diameter dimension of the ferrule 6*a*2.

Then, similarly to the pressing member body 761, the press-fit member 761C is press-fitted into the outer frame 71 in a state in which the end surface of the large diameter portion 7613 on the distal end side abuts on the first positioning surface 711. That is, the press-fit member 761C is fixed in the outer frame 71.

The pressing member body 763 is configured detachably from the press-fit member 761C, and presses the biasing member 75B. The pressing member body 763 includes a plate body having an insertion hole 7631 (FIG. 11) through which a portion of the optical fiber 6a1 on the emission end (ferrule 6a2) side can be inserted. In the fourth embodiment, since four optical fibers 6a1 are provided, four insertion holes 7631 are provided. Then, the pressing member body 763 is fixed to the end surface of the press-fit member 761C on the proximal end side by the fixing member SC (FIGS. 10 and 11) such as a screw in a state in which each optical fiber 6a1 is inserted through each insertion hole 7631. This causes one end (end on distal end side) of the biasing member 75B to abut on the ferrule 6a2, and causes the other end (end on proximal end side) thereof to abut on the plate surface of the pressing member body 763 on the distal end side. Then, the biasing member 75B is pressed by the pressing member body 763 to bias the collimator lens 73B toward the third positioning surface 713 via the ferrule 6a2.

Note that the pressing member body 763 has the same function as the prevention member 762 that prevents inflow of injected resin.

The third positioning surface 713 according to the fourth embodiment corresponds to a positioning surface according to the present disclosure. That is, the collimator lens 73B is pressed toward the distal end side at the ferrule 6a2 by biasing of the biasing member 75B, and the end surface on the distal end side abuts on the third positioning surface 713. Then, the end surface of the collimator lens 73B on the distal end side abuts on the third positioning surface 713, so that the position of the collimator lens 73B in the direction along the central axis Ax is maintained, and the state in which the lens optical axis of the collimator lens 73B is substantially parallel to the central axis Ax is maintained.

According to the above-described fourth embodiment, the following effect is exhibited in addition to effects similar to those in the above-described first embodiment.

In the plug 7C according to the fourth embodiment, the pressing member 76C includes the press-fit member 761C and the pressing member body 763 described above. Therefore, if the pressing member body 763 is removed from the press-fit member 761C, the collimator lens 73B can be replaced with a new collimator lens 73B. Therefore, convenience can be improved.

OTHER EMBODIMENTS

Although the embodiments for carrying out the present disclosure have been described so far, the present disclosure should not be limited only by the above-described first to fourth embodiments.

Not only the plug 7 (7A to 7C) described in the above-described first to fourth embodiments but the receptacle 8 may be adopted as an optical connector according to the present disclosure. Note that a "distal end side" used below when the configuration of the receptacle 8 is described means a side of the plug 7 (7A to 7C) (left side in FIG. 12) connected to the receptacle 8, and a "proximal end side" used below means a side away from the plug 7 (7A to 7C) (side of control device 11, right side in FIG. 12).

Figure 12:
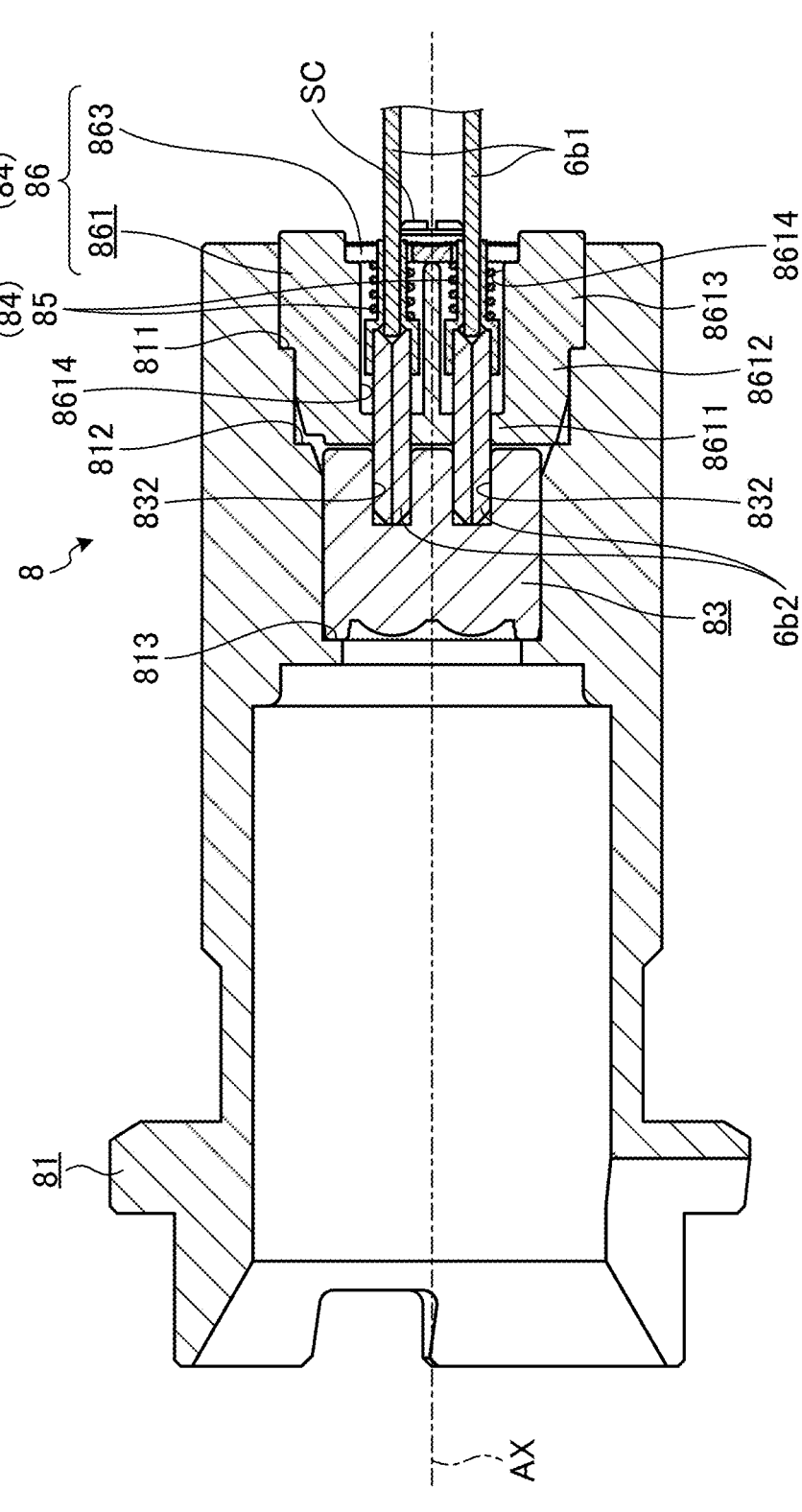
FIG. 12 illustrates a configuration of a receptacle according to a variation of the first to fourth embodiments.
Figure 13:
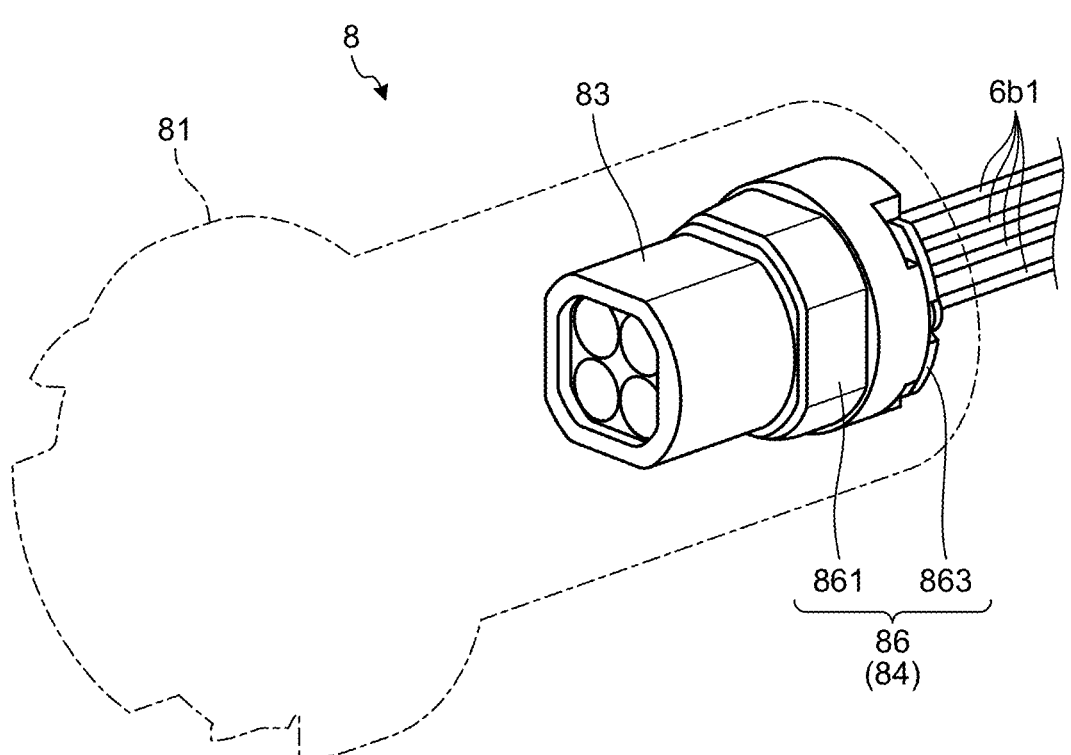
FIG. 13 illustrates the configuration of the receptacle according to the variation of the first to fourth embodiments.

FIGS. 12 and 13 illustrate a configuration of the receptacle 8 according to a variation of the first to fourth embodiments. Specifically, FIG. 12 is a cross-sectional view of the receptacle 8 taken along a plane passing through the central axis Ax of an outer frame 81. FIG. 13 is a perspective view of the receptacle 8 as viewed from the distal end side.

Note that, for convenience of description, only a portion optically connected to the plug 7 (7A to 7C) in the receptacle 8 according to the variation will be described below. FIGS. 12 and 13 also illustrate only the portion. Furthermore, for convenience of description, FIG. 13 illustrates the outer frame 81 with a dot-dashed line.

As illustrated in FIG. 12 or 13, the receptacle 8 according to the variation includes the outer frame 81, the collimator lens 83, and a support mechanism 84.

The outer frame 81 is made of a metal material, and has a substantially circular cylindrical shape as illustrated in FIG. 12 or 13. Note that the shape of the outer frame 81 is not limited to the circular cylindrical shape as long as the outer frame 81 has a cylindrical shape. The outer frame 81 may have a cylinder having another cross-sectional shape. Then, the optical fiber 6b1 constituting the second transmission cable 6b is inserted into the outer frame 81 along the central axis Ax. This causes the outer frame 81 to cover an incident end for an optical signal of the optical fiber 6b1.

Note that the same number of optical fibers 6b1 constituting the second transmission cable 6b as that of the optical fibers 6a1, that is, four optical fibers 6b1 are provided. Then, as illustrated in FIG. 12, each ferrule 6b2 is provided at an incident end for an optical signal of each optical fiber 6b1.

The outer frame 81 has an inner surface having three steps from the proximal end side toward the distal end side and having an inner diameter dimension decreasing stepwise, and has first to third positioning surfaces 811 to 813 similar to the first to third positioning surfaces 711 to 713 described in the above-described first embodiment.

As illustrated in FIG. 12, the collimator lens 83 has the same configuration as the collimator lens 73B described in the above-described third and fourth embodiments. That is, the collimator lens 83 has a recess 832 similar to the recess 732 of the collimator lens 73B. Then, the collimator lens 83 is disposed in the outer frame 81 in a state where the lens optical axis of the collimator lens 83 is substantially parallel to the direction along the central axis Ax. Note that the outer diameter dimension of the collimator lens 83 is slightly smaller than the inner diameter dimension of the second positioning surface 712 (outer diameter dimension of the third positioning surface 713). That is, the collimator lens 83 is disposed in a state of having predetermined clearance between the collimator lens 83 and the inner surface of the outer frame 81 in a radial direction centered on the central axis Ax.

Then, the collimator lens 83 is a single lens facing incident ends of the four optical fibers 6b1, and collects an optical signal (collimated light) emitted from the collimator lens 73 (73B) in the plug 7 (7A to 7C) to each incident end of each optical fiber 6b1.

The support mechanism 84 is provided in the outer frame 81, and maintains the posture of the collimator lens 83 in the outer frame 81. The support mechanism 84 has a configuration similar to that of the support mechanism 74C described in the above-described fourth embodiment. That is, the support mechanism 84 includes a biasing member 85 and a pressing member 86 (press-fit member 861 (including small diameter portion 8611, pressing portion 8612, large diameter portion 8613, and storage hole 8614) and pressing member body 863 (including insertion hole (not illustrated))) similar to the biasing member 75B and the pressing member 76C (including press-fit member 761C (including small diameter portion 7611, pressing portion 7612, large diameter portion 7613, and storage hole 7614) and pressing member body 763 (including insertion hole 7631)) of the support mechanism 74C.

Then, the press-fit member 861 is press-fitted into the outer frame 81 in a state in which the end surface of the large diameter portion 8613 on the distal end side abuts on a first positioning surface 811. That is, the press-fit member 861 is fixed in the outer frame 81. Furthermore, the pressing member body 863 is fixed to the end surface of the press-fit member 861 on the proximal end side by the fixing member SC (FIG. 12) such as a screw in a state in which each optical fiber 6b1 is inserted through each insertion hole (not illustrated). This causes one end (end on distal end side) of the biasing member 85 to abut on the ferrule 6b2, and causes the other end (end on proximal end side) thereof to abut on the plate surface of the pressing member body 863 on the distal end side. Then, the biasing member 85 is pressed by the pressing member body 863 to bias the collimator lens 83 toward a third positioning surface 813 via the ferrule 6b2.

The third positioning surface 813 according to the variation corresponds to a positioning surface according to the present disclosure. That is, the collimator lens 83 is pressed toward the distal end side at the ferrule 6b2 by biasing of the biasing member 85, and the end surface on the distal end side abuts on the third positioning surface 813. Then, the end surface of the collimator lens 83 on the distal end side abuts on the third positioning surface 813, so that the position of the collimator lens 83 in the direction along the central axis Ax is maintained, and the state in which the lens optical axis of the collimator lens 83 is substantially parallel to the central axis Ax is maintained.

Note that, although, in the variation, a configuration similar to the support mechanism 74C described in the above-described fourth embodiment is adopted as the support mechanism 84, this is not a limitation. A configuration similar to the support mechanisms 74, 74A, and 74B described in the above-described first to third embodiments may be adopted. Note that, when a configuration similar to the support mechanisms 74 and 74A is adopted as the support mechanism 84, the collimator lens 83 also adopts a configuration similar to the collimator lens 73 described in the above-described first embodiment.

In the variation described in the above-described first to fourth embodiments and FIGS. 12 and 13, the collimator lenses 73, 73B, and 83 may be made of a material such as glass in addition to a resin material.

Although, in the above-described first to fourth embodiments, the medical observation system 1 having the insertion portion 2 configured by a rigid endoscope is adopted as a medical device according to the present disclosure, this is not a limitation. For example, a medical observation system having the insertion portion 2 configured by a flexible endoscope may be adopted as the medical device according to the present disclosure. Furthermore, a medical observation system such as a surgical microscope (e.g., see JP 2016-42981 A) for magnifying and observing a predetermined visual field area in a subject (living body) or on the surface of the subject (surface of living body) may be adopted as the medical device according to the present disclosure.

Note that the following configurations also belong to the technical scope of the present disclosure.

(1) An optical connector including: an outer frame, having a cylindrical shape, into which a part of an optical transmission line for transmitting an optical signal is inserted, the outer frame covering an incident end or an emission end for an optical signal of the optical transmission line; a collimator lens provided in the outer frame and facing the incident end or the emission end; and a support mechanism that is disposed in the outer frame and that maintains a posture of the collimator lens in the outer frame, wherein a positioning surface that abuts on the collimator lens to maintain the posture of the collimator lens in the outer frame is provided in the outer frame, and the support mechanism includes: a biasing member; and a pressing member that presses the biasing member and biases the collimator lens toward the positioning surface with the biasing member.

(2) The optical connector according to (1), wherein the biasing member abuts on the collimator lens.

(3) The optical connector according to (2), wherein the pressing member is press-fitted into the outer frame.

(4) The optical connector according to (2), wherein the pressing member includes: a pressing member body that presses the biasing member; and a regulating member that is configured detachably from the outer frame and that regulates movement of the collimator lens toward a direction opposite to a biasing direction caused by the biasing member in the pressing member body.

(5) The optical connector according to (1), wherein a ferrule is provided at the incident end or the emission end of the optical transmission line, and the biasing member abuts on the ferrule, and biases the collimator lens toward the positioning surface via the ferrule.

(6) The optical connector according to (5), wherein the pressing member is press-fitted into the outer frame.

(7) The optical connector according to (5), wherein the pressing member includes: a press-fit member press-fitted into the outer frame; and a pressing member body that is configured detachably from the press-fit member and that presses the biasing member.

(8) The optical connector according to any one of (1) to (7), wherein the positioning surface intersects a central axis of the outer frame.

(9) The optical connector according to any one of (1) to (8), wherein the collimator lens is made of a resin material.

(10) The optical connector according to any one of (1) to (9), wherein a plurality of optical transmission lines is disposed in parallel in the outer frame, and the collimator lens is a single lens facing the respective incident ends and the respective emission ends of the plurality of optical transmission lines.

(11) A medical device including: a medical observation device that images a subject and generates a captured image; two transmission cables in each of which an optical transmission line for transmitting an optical signal based on the captured image is disposed; and an optical connector that mechanically and optically connects the two transmission cables with each other, wherein the optical connector includes: an outer frame, having a cylindrical shape, into which a part of the optical transmission line is inserted, the outer frame covering an incident end or an emission end for an optical signal of the optical transmission line; a collimator lens provided in the outer frame and facing the incident end or the emission end; and a support mechanism that is disposed in the outer frame and that maintains a posture of the collimator lens in the outer frame, a positioning surface that abuts on the collimator lens to maintain the posture of the collimator lens in the outer frame is provided in the outer frame, and the support mechanism includes: a biasing member; and a pressing member that presses the biasing member and biases the collimator lens toward the positioning surface with the biasing member.

REFERENCE SIGNS LIST

1 MEDICAL OBSERVATION SYSTEM
2 INSERTION PORTION
3 LIGHT SOURCE DEVICE
4 LIGHT GUIDE
5 CAMERA HEAD
6a FIRST TRANSMISSION CABLE
6a1 OPTICAL FIBER
6a2 FERRULE
6b SECOND TRANSMISSION CABLE
6b1 OPTICAL FIBER
6b2 FERRULE
7, 7A to 7C PLUG
8 RECEPTACLE
9 DISPLAY DEVICE
10 THIRD TRANSMISSION CABLE
11 CONTROL DEVICE
12 FOURTH TRANSMISSION CABLE
21 EYEPIECE PORTION
71 OUTER FRAME
72 COVER MEMBER
73, 73B COLLIMATOR LENS
74, 74A to 74C SUPPORT MECHANISM
75, 75B BIASING MEMBER
76, 76A, 76C PRESSING MEMBER
77 PRESSING MEMBER BODY
78 REGULATING MEMBER
78a SCREWING STRUCTURE
81 OUTER FRAME
83 COLLIMATOR LENS
84 SUPPORT MECHANISM
85 BIASING MEMBER
86 PRESSING MEMBER
711 FIRST POSITIONING SURFACE
712 SECOND POSITIONING SURFACE
713 THIRD POSITIONING SURFACE
714 ATTACHMENT PORTION
730 LENS BODY
731 PROJECTING PORTION
732 RECESS
761 PRESSING MEMBER BODY
761C PRESS-FIT MEMBER
762 PREVENTION MEMBER
763 PRESSING MEMBER BODY
771 SEALING MATERIAL
811 FIRST POSITIONING SURFACE
812 SECOND POSITIONING SURFACE
813 THIRD POSITIONING SURFACE
832 RECESS
861 PRESS-FIT MEMBER
863 PRESSING MEMBER BODY
7611 SMALL DIAMETER PORTION
7612 PRESSING PORTION
7613 LARGE DIAMETER PORTION
7614 STORAGE HOLE
7614a LARGE DIAMETER HOLE
7614b SMALL DIAMETER HOLE
7615 INSTALLATION HOLE
7621 CUTOUT
7631 INSERTION HOLE
8611 SMALL DIAMETER PORTION

8612 PRESSING PORTION
8613 LARGE DIAMETER PORTION
8614 STORAGE HOLE
Ax CENTRAL AXIS
Bx, Bx' LENS OPTICAL AXIS
SC FIXING MEMBER

The invention claimed is:

1. An optical connector comprising:
an outer frame, having a cylindrical shape, into which a part of an optical transmission line for transmitting an optical signal is inserted, the outer frame covering an incident end or an emission end for an optical signal of the optical transmission line;
a collimator lens provided in the outer frame and facing the incident end or the emission end; and
a support mechanism that is disposed in the outer frame and that maintains a posture of the collimator lens in the outer frame,
wherein a positioning surface that abuts on the collimator lens to maintain the posture of the collimator lens in the outer frame is provided in the outer frame, and
the support mechanism includes:
a biasing member; and
a pressing member that presses the biasing member and biases the collimator lens toward the positioning surface with the biasing member.

2. The optical connector according to claim 1, wherein the biasing member abuts on the collimator lens.

3. The optical connector according to claim 2, wherein the pressing member is press-fitted into the outer frame.

4. The optical connector according to claim 2, wherein the pressing member includes:
a pressing member body that presses the biasing member; and
a regulating member that is configured detachably from the outer frame and that regulates movement of the collimator lens toward a direction opposite to a biasing direction caused by the biasing member in the pressing member body.

5. The optical connector according to claim 1, wherein
a ferrule is provided at the incident end or the emission end of the optical transmission line, and
the biasing member abuts on the ferrule, and biases the collimator lens toward the positioning surface via the ferrule.

6. The optical connector according to claim 5, wherein the pressing member is press-fitted into the outer frame.

7. The optical connector according to claim 5, wherein the pressing member includes:
a press-fit member press-fitted into the outer frame; and
a pressing member body that is configured detachably from the press-fit member and that presses the biasing member.

8. The optical connector according to claim 1, wherein the positioning surface intersects a central axis of the outer frame.

9. The optical connector according to claim 1, wherein the collimator lens is made of a resin material.

10. The optical connector according to claim 1, wherein
a plurality of optical transmission lines is disposed in parallel in the outer frame, and
the collimator lens is a single lens facing the respective incident ends and the respective emission ends of the plurality of optical transmission lines.

11. A medical device comprising:
a medical observation device that images a subject and generates a captured image;

two transmission cables in each of which an optical
  transmission line for transmitting an optical signal
  based on the captured image is disposed; and
an optical connector that mechanically and optically con-
  nects the two transmission cables with each other,
wherein the optical connector includes:
  an outer frame, having a cylindrical shape, into which
    a part of the optical transmission line is inserted, the
    outer frame covering an incident end or an emission
    end for an optical signal of the optical transmission
    line;
  a collimator lens provided in the outer frame and facing
    the incident end or the emission end; and
  a support mechanism that is disposed in the outer frame
    and that maintains a posture of the collimator lens in
    the outer frame,
  a positioning surface that abuts on the collimator lens
    to maintain the posture of the collimator lens in the
    outer frame is provided in the outer frame, and
the support mechanism includes:
  a biasing member; and
  a pressing member that presses the biasing member and
    biases the collimator lens toward the positioning
    surface with the biasing member.

* * * * *